United States Patent [19]

Witty et al.

[11] 4,456,689

[45] Jun. 26, 1984

[54] COMPETITIVE PROTEIN BINDING ASSAY USING AN ORGANOSILANE-SILICA GEL SEPARATION MEDIUM

[75] Inventors: Thomas R. Witty, Sandy; Mark E. Astill, Holladay, both of Utah

[73] Assignee: Becton Dickinson and Company, Paramus, N.J.

[21] Appl. No.: 379,227

[22] Filed: May 17, 1982

[51] Int. Cl.³ .................... G01N 33/58; G01N 33/60; G01N 33/74; G01N 33/78
[52] U.S. Cl. .................................... 436/500; 436/504; 436/505; 436/541; 436/542; 436/804; 436/824
[58] Field of Search .................... 424/1; 436/541, 538, 436/500, 542, 804, 824; 528/32-38

[56] References Cited

U.S. PATENT DOCUMENTS

| | | | |
|---|---|---|---|
| 4,173,571 | 11/1979 | Chabala et al. | 260/343.41 |
| 4,180,642 | 12/1979 | Takago | 528/32 |
| 4,201,881 | 5/1980 | De Luca et al. | 568/819 |
| 4,223,131 | 9/1980 | De Luca et al. | 542/428 |
| 4,241,062 | 12/1980 | Hannah | 424/151 |
| 4,248,992 | 2/1981 | Takago | 528/28 |
| 4,265,634 | 5/1981 | Pohl | 23/230 R |
| 4,360,471 | 11/1982 | De Luca et al. | 260/397.2 |

OTHER PUBLICATIONS

Tabor, M. W. et al., Int. J. Envir. Analyt. Chem., vol. 8, pp. 197-215 (1980).
Hsiung, H. M. et al., Clinical Biochemistry, vol. 11 (2), pp. 54-56 (1978) Abstract.

Primary Examiner—Benjamin R. Padgett
Assistant Examiner—M. Moskowitz

[57] ABSTRACT

An improved competitive protein binding assay comprising; incubating an analyte in the presence of labeled analyte and a protein binder suitable for competitive binding activity by the analyte and the labeled analyte to provide a mixture having free analyte, free labeled analyte, bound analyte and bound labeled analyte, substantially separating the bound analyte and the bound labeled analyte from the free analyte and free labeled analyte to form a first fraction containing substantially the bound analyte and the bound labeled analyte and a second fraction containing substantially the free analyte and the free labeled analyte by causing a predetermined level of the mixture to flow through a bed of an organosilane coupled to silica gel, and detecting the labeled analyte of at least one of the first and second fractions to determine the concentration of the analyte by comparison to a reference.

13 Claims, 6 Drawing Figures

COMPETITIVE PROTEIN BINDING ASSAY USING AN ORGANOSILANE-SILICA GEL SEPARATION MEDIUM

BACKGROUND OF THE INVENTION AND PRIOR ART

The present invention relates to competitive protein binding assay, and more particularly, to competitive protein binding assay for various low molecular weight ligands such as digoxin, $T_3$ uptake, thyroxine, cortisol, insulin and for simultaneous determination of folate and vitamin $B_{12}$.

Generally, it is well known to measure endogenous low molecular weight ligands such as folate or vitamin $B_{12}$ by a competitive protein-binding technique. For example, competitive protein-binding for the assay of either folate or vitamin $B_{12}$ involves the ability of unlabeled folate or vitamin $B_{12}$ in serum or other media to compete with a known quantity of labeled folic acid or labeled vitamin $B_{12}$ for specific sites on a folate protein binder or vitamin $B_{12}$ protein binder and thereby inhibit the binding of the labeled folic acid or vitamin $B_{12}$. As a result of the competitive inhibition, the ratio of bound labeled folic acid or vitamin $B_{12}$ to free labeled folic acid or vitamin $B_{12}$ diminishes as the concentration of unlabeled folate or vitamin $B_{12}$ is increased. Accordingly, the concentration of folate or vitamin $B_{12}$ in an unknown sample, such as a patient's serum, is obtained by comparing the inhibition (ratio of bound labeled folic acid or vitamin $B_{12}$ to free labeled folic acid or vitamin $B_{12}$) observed with that produced by known amounts of folate or vitamin $B_{12}$, as presented in a standard curve. Such measurements generally require successive runs for the determination of folate and of vitamin $B_{12}$.

U.S. Pat. No. 4,146,602 to Gutcho et al. describes a method for the simultaneous radioassay of folate and vitamin $B_{12}$. In the method of the Gutcho patent, a sample containing folate and vitamin $B_{12}$, free of endogenous binder therefor, is contacted with a protein binder for the folate, a separate protein binder for the vitamin $B_{12}$, a folate tracer labeled with radioiodine and a vitamin $B_{12}$ tracer labeled with radiocobalt. The bound portions of folate and vitamin $B_{12}$ are then separated from the free portions of folate and vitamin $B_{12}$. The radioactivity of at least one of the bound and free portions is then counted and compared to standard curves to determine both the folate concentration and the vitamin $B_{12}$ concentration. Of course, separate counts are required to determine radioiodine and radiocobalt.

As described in the Gutcho et al. patent the bound and free portions of the folate and vitamin $B_{12}$ are separated by procedures known in the art. Such procedures, as described in the Gutcho et al. patent generally rely on the use of a particulate adsorbent. The sample containing the bound and free portions of labeled and unlabeled folate and vitamin $B_{12}$ are mixed with the particulate adsorbent. The mixture of adsorbent and sample is maintained at room temperature, usually under turbulent conditions, for a period of time to permit contact of the labeled folate and vitamin $B_{12}$ with the particulate adsorbent. The mixture of sample and particulate adsorbent is then centrifuged for a period of time, usually about 15 minutes, and the sample is separated into bound and unbound portions by decanting the unbound portion from the bound portion retained by the adsorbent.

The Gutcho et al. patent indicates that various adsorbents, such as ion exchange resins and inorganic adsorbents can be used to separate the bound and unbound portions. The only adsorbent mentioned, however, is dextran coated charcoal. Such reference to a variety of useful adsorbents, moreover, is in the context of the separation method used in the Gutcho et al. patent, i.e., a batch separation requiring a lengthy contact period and centrifugation.

It would be desirable to adapt a competitive protain binding assay, such as a simultaneous $B_{12}$/folate assay system to the automated methods available for separating bound and unbound fractions. Such automated systems utilize a continuous stream of a treated sample which is passed through a column containing a separation medium capable of removing the unbound fraction from the sample by antibody/antigen coupling, adsorption or other physical means. Such systems are usually provided with automatic counters capable of counting both radioiodine and radiocobalt and also capable of monitoring both the free and bound fraction through successive use of a coupling buffer and an elution buffer. An integrated program is then used to provide a direct readout in terms of percent bound. The percent which is bound to the separation medium in the column is then related to standard curves to provide a measure of the concentration of folate, vitamin $B_{12}$ or other analyte present in the sample.

To be useful in a radioassay system, the binding material must have a high separation efficiency (maximum binding of free fraction) as well as stability and the ability to be eluted for counting of the bound fraction and recovery of the resin for future runs. In respect to competitive protein binding assays, the separation medium must also have a low affinity for the protein in the sample matrix and the protein used to effect competitive binding of labeled and unlabeled analyte. Surprisingly, the separation media most extensively used in competitive protein binding radioassay systems have not been found to be suitable for the simultaneous assay of folate and vitamin $B_{12}$. The dextran coated charcoal described in the Gutcho et al. patent was found to work well in an aqueous environment but provided poor maximum binding with the sample in a protein matrix, such as serum.

SUMMARY OF THE INVENTION

In accordance with the present invention, it has been determined that an organosilane coupled to silica gel is highly useful as a separation medium for competitive protein binding assays and is particularly useful for the competitive protein binding radioassay of various analytes including the simultaneous assay of folate and vitamin $B_{12}$ in an automated system. Competitive protein binding assays allow specific detection and quantitation of extremely low levels ($10^{-14}$ moles) of the desired analyte. Unlike direct analysis where the sensitivity of the system is limited by the detection limit of the native compound, sensitivity of competitive protein binding, which is an indirect method, is greatly enhanced by the use of the labeled tracer which competes with the endogenous analyte for the limited binding sites on a high affinity binding protein. A necessary feature for a competitive protein binding assay is a convenient method for distinguishing the protein bound fraction from the unbound (free) fraction. This is typically done by physical separation of the two fractions. The physical separation of the two fractions in an automated system, however, requires that the separation medium have a high separation efficiency over a short interval of time.

Generally, the present invention is directed to an improved competitive protein binding assay. The assay includes the steps of incubating an analyte in the presence of an analyte tracer labeled with a radioisotope and a protein binder. The protein binder is suitable for competitive binding activity by the analyte and the analyte tracer to provide a prepared sample having free analyte, free analyte tracer, bound analyte and bound analyte tracer. The free analyte and free analyte tracer are then separated from the bound analyte and bound analyte tracer to form a first fraction containing substantially the free analyte and the free analyte tracer and a second fraction containing substantially the bound analyte and the bound analyte tracer. The separation is effected by causing a predetermined level of the prepared sample to flow through a bed of an organosilane coupled to silica gel. Thereafter, the radioactivity of at least one of the first and the second fraction is counted to determine the concentration of the analyte by comparison of the radioactive count to standard curves.

Accordingly, it is the principal object of the present invention to provide an improved competitive protein binding assay for various analytes.

It is another object of the present invention to provide an improved competitive protein binding assay for various analytes which is adapted to be used in an automated system.

It is a still further object of the present invention to provide a cartridge for use in an automated system which contains a separating medium adapted for use in an improved competitive binding assay for various analytes.

It is a further object of the present invention to provide a competitive protein binding assay adapted for the simultaneous determination of folate and vitamin $B_{12}$.

It is a still further object of the present invention to provide an automated radioassay for simultaneous determination of folate and vitamin $B_{12}$.

These and other objects will become more apparent from the following detailed description and the accompanying drawings.

THE DRAWINGS

DETAILED DESCRIPTION OF THE INVENTION

As indicated hereinabove, various features of the present invention are particularly adapted to the simultaneous radioassay of folate and vitamin $B_{12}$. The further detailed description container hereinbelow describes various features in respect to the simultaneous radioassay of folate and vitamin $B_{12}$. It should be understood, however, that the present invention is suitable for other competitive protein binding assays as described in the examples and appended claims.

Generally, in accordance with one embodiment of the present invention, a sample containing folate and vitamin $B_{12}$ is treated to release the folate and vitamin $B_{12}$ from their endogenous binders. The sample containing released folate and vitamin $B_{12}$ is contacted with a binder for the folate, a binder for the vitamin $B_{12}$, a folate tracer labeled with a first radioactive isotope and a vitamin $B_{12}$ tracer labeled with a second radioactive isotope. The sample, containing folate, vitamin $B_{12}$, binders for folate and vitamin $B_{12}$, and tracers for folate and vitamin $B_{12}$ is then incubated resulting in competitive binding between the labeled and unlabeled folate and the labeled and unlabeled vitamin $B_{12}$ for their respective binder sites. The bound portions of labeled and unlabeled folate and bound portions of labeled and unlabeled vitamin $B_{12}$ are simultaneously separated from the free portions of labeled and unlabeled folate and the free portions of labeled and unlabeled vitamin $B_{12}$ by causing the prepared sample to flow through a bed of silica gel coated with an organosilane. Thereafter the radioactivity of at least one of the bound or free portions is counted and the amounts of folate and vitamin $B_{12}$ are determined from standard curves.

Figure 1:
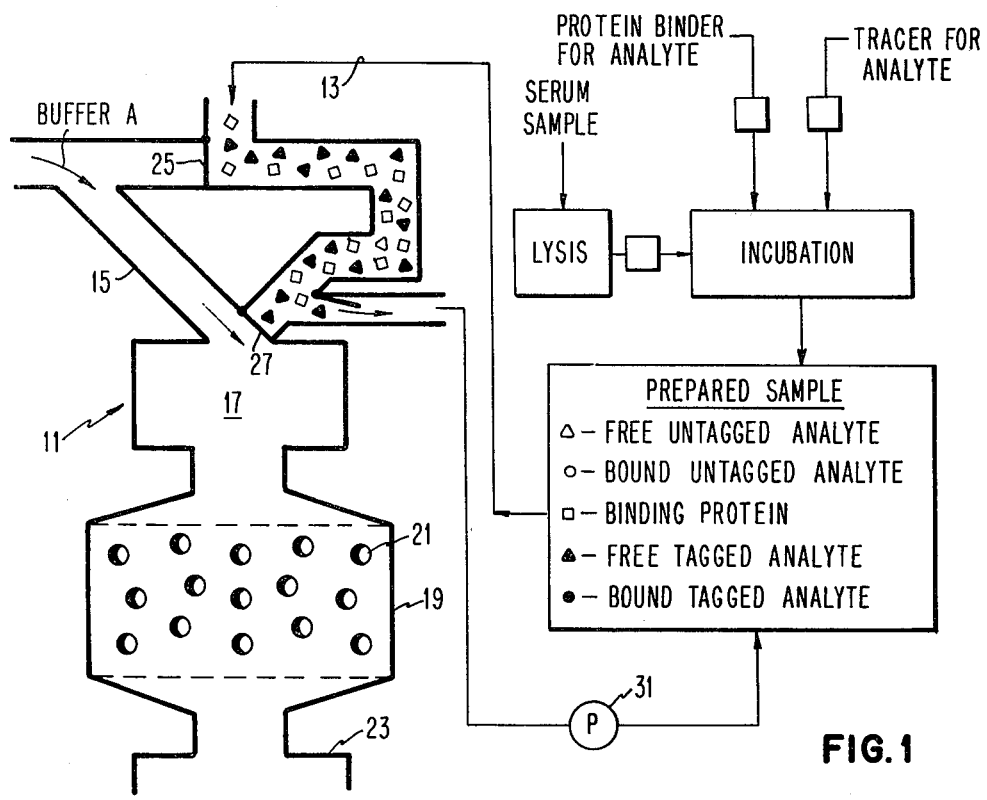
FIG. 1 is a schematic diagram of an automated radioassay system showing a flow chart depicting various steps in the preparation of a blood serum sample for competitive protein binding assay of vitamin $B_{12}$ and folate.

As shown in FIG. 1, the serum sample first undergoes lysis to release the folate and vitamin $B_{12}$ from their endogenous binders. Incubation then occurs in the presence of a protein binder for folate, a protein binder for vitamin $B_{12}$, a tracer for folate and a tracer for vitamin $B_{12}$. This provides a prepared sample which is continuously pumped through a sample loop in an automated radioassay system 11. As shown in FIG. 1, the prepared sample is depicted in the various forms of a single analyte which could be either $B_{12}$, folate or other analyte. Of course, both analytes are present in the prepared sample in the indicated forms.

The automated radioassay system 11 includes a prepared sample loop 13, a buffer bypass zone 15, a prefilter-Peltier cooler 17 a separating chamber 19 containing a separating medium 21 and a radioactive detector 23, two-way valves 25 and 27 are used for routing the prepared sample and various buffer solutions in a predetermined cycle and one-way valve 29 is used in prepared sample routing and rinse solution routing.

While the steps of lysis, incubation and holding of the prepared sample are shown as separate blocks in the schematic outline of FIG. 1, it should be understood that these various steps in providing a prepared sample can take place in a single container and the steps can be automated to provide a completely integrated automated system for competitive protein binding assay.

Figure 2:
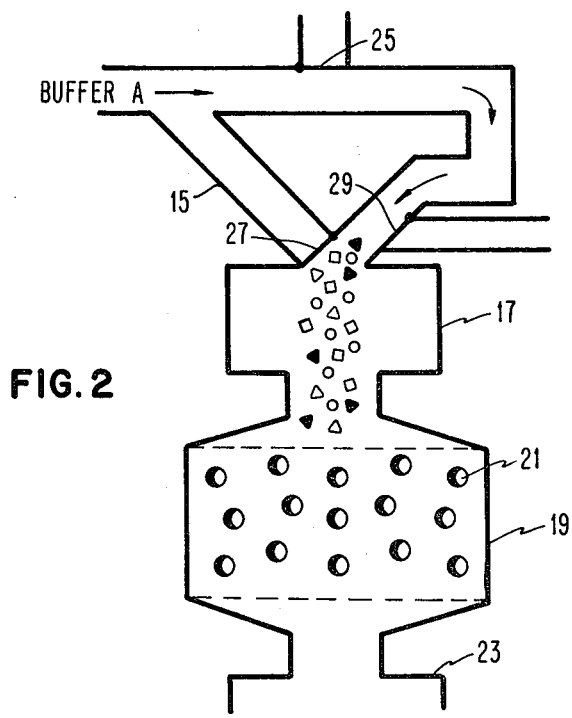
FIGS. 2 through 6 show various steps and positions of the automated radioassay system during the radioassay.

As shown in FIG. 1, valves 25, 27 and 29 are set so that buffer A (sometimes referred to herein as the adsorption buffer) is passed through the separating chamber over the separating medium to rinse the system preparatory to processing the prepared sample. The arrangement of the valves is such that the prepared sample is continuously flowed through the sample loop 13. In FIG. 2, the valves 26 and 27 are switched to block passage of buffer A directly to the separating chamber and to route buffer A into the sample loop. Valve 29 is simultaneously closed so that buffer A carries the prepared sample in the sample loop past the Peltier cooler 17 to the separating chamber 19.

The simultaneous switching of valve 25 and valve 29 entraps a known volume of prepared sample and causes the known volume of prepared sample to flow through the bed of separating medium 21 contained in separating chamber 19. While buffer A (adsorption buffer) is flowing a portion of the free tagged and untagged analyte becomes bound to the separating medium. An important feature of the present invention is the discovery that the mass flow rate of the prepared sample through the separating medium is related to the efficiency of binding of the free tagged and untagged analyte. That is, the maximum percent bound of the free tagged and untagged analyte increases to an optimum at a certain mass flow rate. In general, it is desirable to have mass flow rates of from about 0.01 to 0.20 ml of sample per milligram of separating medium (range 25–1000 mg) volume per minute and preferably a mass flow rate of from about 0.07 to about 0.10 ml/cc/min. (range 50–150 mg) of separation medium.

Figure 3:
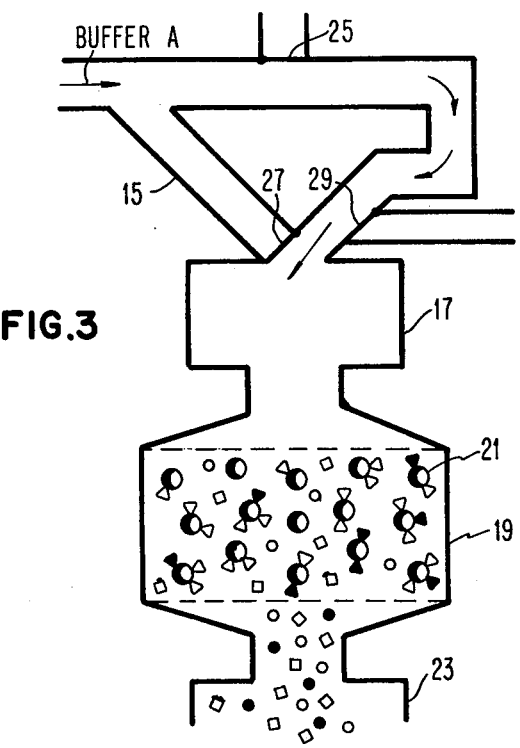

As shown in FIG. 3, the flow of buffer A is continued so as to carry the bound tagged and untagged analyte and the residual binding protein through the radioactive detector so that a count can be made of the bound tagged analyte.

Figure 4:
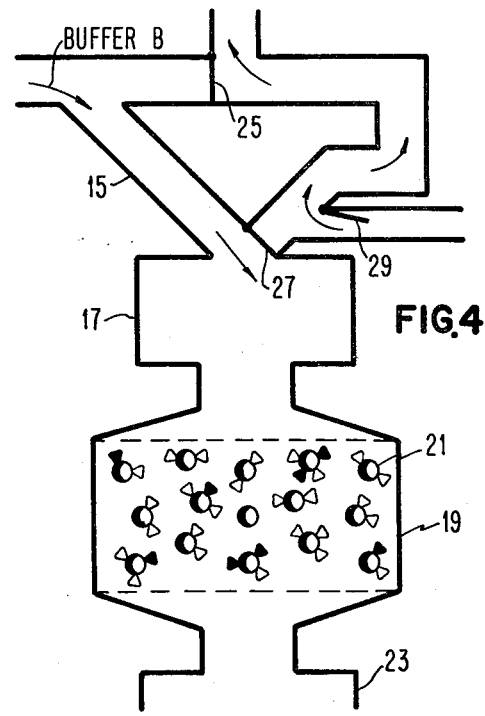
Figure 5:
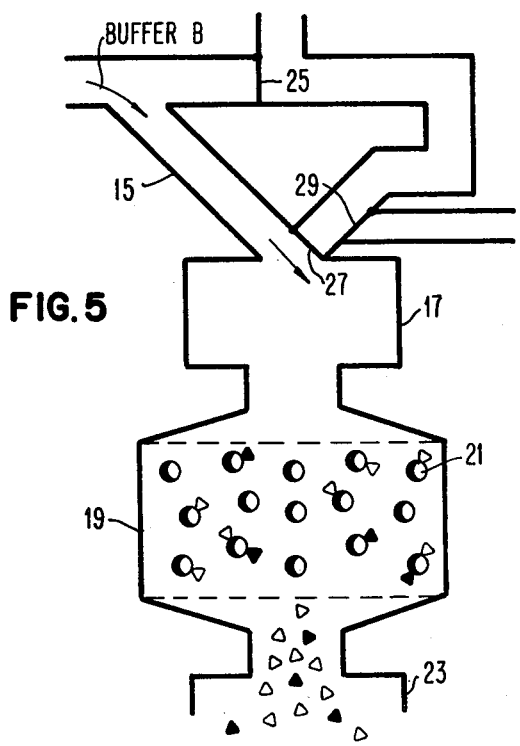
Figure 6:
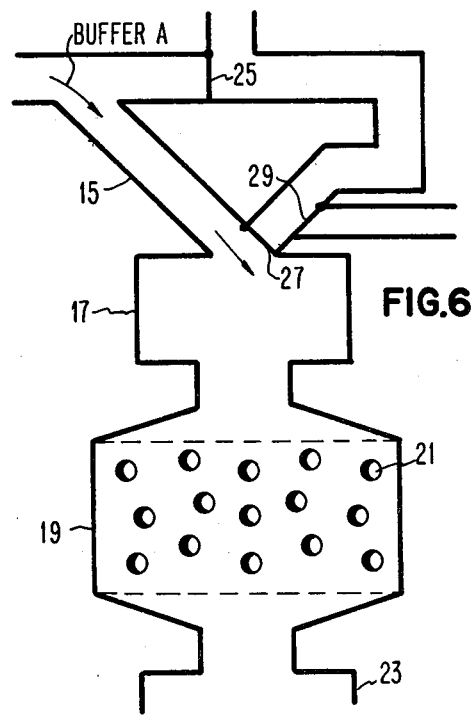

As shown in FIG. 4, valves 25, 27 and 29 have been placed in their original position of FIG. 1. A rinse solution is counterflowed into the sample loop from the sample pump 31. Buffer B (sometimes referred to herein as an elution buffer) is introduced into the buffer bypass 15 in order to release the free analyte which became bound to the separating medium during flow of buffer A. The rinse solution is stopped and the flow of buffer B is continued, as shown in FIG. 5, to cause the release of the free analyte that became bound to the separating medium for counting in the detector. Thus, the automated assay system of the present invention permits easy counting of both the materials which passes through the separating medium (bound) during flow of buffer A and the material which became bound to the separating medium (free) which is released during the flow of buffer B so that a total count of all material can be integrated to provide a more accurate radioassay. As shown in FIG. 6, buffer B is terminated and buffer A rinses the system to eliminate residual buffer B and to prepare the separating chamber for the next cycle.

Referring again specifically to a simultaneous radioassay for folate and vitamin $B_{12}$, folate and vitamin $B_{12}$ are released from endogenous binders by heating a sample, containing folate and vitamin $B_{12}$; e.g., a serum or plasma sample with the endogenous binders being destroyed by such heating. The heating can be effected at a wide variety of pH values, with the pH generally being 5 or greater. The pH is most generally at least 7.0 (neutral or alkaline pH), with the pH preferably being at least 9.0 and preferably no greater than 9.6. The most preferred pH is from 9.2 to 9.4 (generally 9.3) in that this permits the release to be effected at the same pH as the subsequent assay in which folic acid is employed as a standard, instead of the reduced methyl derivative of folic acid. The heating to release vitamin $B_{12}$ and folate from their endogenous binders is generally effected at a temperature of from about 95° C. to about 110° C., and preferably of from about 98° C. to about 105° C.

The release of folic acid and vitamin $B_{12}$ from their endogenous binders is also effected in the presence of a suitable reducing agent in order to preserve the endogenous folate present in the serum in reduced form. The reducing agent which is included during the heating step is a reducing agent which maintains the reduced folate without adversely affecting the vitamin $B_{12}$ and which is stable under the assay conditions. Examples of suitable reducing agents include ascorbate, Cleland's reagent (dithiothreitol); dithioerythritol; monothioglygol; thiodiglycol; thioglycollic acid; cysteine, homocysteine, gluthathione; mercaptoethanol; sulfhydryl reducing agents; inorganic reducing agents, such as sodium sulfite; sodium dithionite; sodium sulfide, sodium metabisulfite, with the organic reducing agents being preferred.

After release of folic acid and vitamin $B_{12}$ from their endogenous binders and destruction of such endogenous binders, the sample is contacted with a dual tracer; i.e., a tracer for folate and a tracer for vitamin $B_{12}$, and a dual binder; i.e., a protein binder for folate and a protein binder for vitamin $B_{12}$. The binders, both naturally occurring and antibodies, for folate are well known in the art, and any one of such binders may be employed in the assay of the present invention. Representative examples of such binders, include binders extracted from various animal organs particularly kidneys and pancreas; B-lactoglobulin preparations; cow's milk, dolphin serum and the like, with milk binder being preferred. Similarly, binders for vitamin $B_{12}$ are well known in the art. Suitable binders include saliva, chicken serum and intrinsic factor, with the preferred binder being intrinsic factor.

The folate tracer is either folic acid (pteroylmonoglutamine acid (PGA) [or the reduced 5-methyl derivative of folic acid, 5-methyltetrahydrofolic acid (MTFA)] or appropriate analogs thereof, labeled with a radioactive isotope, which is preferably a radioactive isotope of iodine. The term folate tracer generically refers to radiolabeled folic acid, the radiolabeled reduced 5-methyl derivative and the radiolabeled analogs thereof. The 5-methyl derivative is generally not employed as a tracer due to problems of instability. The radiolabeled folate employed as a tracer is preferably radiolabeled folic acid and the term radiolabeled folic acid includes the radiolabeled analogs thereof; i.e., folic acid substituted with a radiolabeled radical. The preferred radioactive isotope is a radioactive isotope of iodine, and most preferably $I^{125}$. The tracer is usually a folic acid including a substituent which includes a radioiodinated phenol or imidazole group such as histidine, histamine, tyrosine or tyramine, which is substituted with a radioactive isotope of iodine. A particularly preferred tracer is one in which the $\alpha$ carboxyl group of the glutamyl moiety is substituted with radioiodinated tyrosyl or histidyl. However, it is to be understood that the tracer can also be one in which the $\gamma$ carboxyl group is so substituted, as disclosed in U.S. Pat. No. 3,989,812.

The vitamin $B_{12}$ tracer is preferably a radiolabeled vitamin $B_{12}$, with the vitamin $B_{12}$ preferably being labeled with $^{57}Co$.

In accordance with the preferred procedure, the assay is effected at an alkaline pH; i.e., the assay and release of folate and vitamin $B_{12}$ from binders are both effected at alkaline pH, with the release being effected at temperatures known in the art; i.e., generally in the order of from about 98° C. to 105° C. It is to be understood that the release and subsequent assay could be effected at different pH values; however, identical pH values are preferably employed in that this eliminates the necessity for a pH adjustment.

In accordance with the most preferred procedure for effecting the assay, folate and vitamin $B_{12}$ are released from their endogenous binders at an alkaline pH of from about 9.2 to 9.4 followed by effecting the assay at a pH of from about 9.2 to about 9.4 with the folate tracer being in the form of a radioiodinated folic acid, with the radioiodinated folic acid preferably being a radioiodinated analog of folic acid; e.g., radioiodosubstituted histidyl, tyrosyl or tyramyl, preferably tyrosyl. The tracer for vitamin $B_{12}$ is $^{57}Co$ labeled vitamin $B_{12}$. The use of radiolabeled folic acid and assay of endogenous folates at such a pH permits the use of folic acid as a standard, instead of MTFA, as described in U.S. Pat. No. 3,988,431.

It is to be understood that in accordance with the preferred procedure wherein folic acid is employed as a standard, even though the assay is effected at pH 9.2–9.4, the release from the separating medium can be effected at another pH value. Similarly, if the standard for the assay is MTFA, the assay and/or releas can be effected at pH values other than 9.2–9.4.

The bound and free portions are separated by flowing a predetermined volume of the prepared sample over a bed of silica gel which is coupled by covalent bonding or other means with an organosilane. Generally, the organosilane has an aliphatic $C_8$–$C_{24}$ organic moiety. A particularly preferred organosilane is octadecylsilane (ODS). The silica gel preferably has a particle size of from about 25 to about 250 microns.

The organosilane-silica gel separating medium is preferably disposed in a cartridge comprising a chamber with an inlet opening and an outlet opening for use in an automated assay system. The chamber shape is preferably cylindrical, although other shapes can be used, with a length of from about 5 to about 20 mm and a diameter of from about 2 to about 8 mm, most preferably a length of 12 mm and a diameter of 4 mm. The separating medium is preferably present in the chamber at a level of from about 50 to about 150 mg, most preferably about 95 mg.

The flow rate of the preprared sample through the organosilane-silica gel bed is preferably from about 0.01 to about 0.20 ml/cc/min. most preferably from about 0.07 to about 0.10 ml/cc/min.

As should be apparent, since different radioactive isotopes are employed for labeling the folate tracer and vitamin $B_{12}$ tracer, the respective tracers may be counted in different channels of a counter or if the counter has one channel, it can be calibrated so that different counter settings will count one isotope at a time.

The following examples further illustrate various features of the invention but is not intended to limit the scope of the invention which is defined in the appended claims.

EXAMPLE 1

Simultaneous Vitamin $B_{12}$ and Folate

The simultaneous determination of vitamin $B_{12}$ and Folic Acid is accomplished by adding 100 ul of a serum or test sample to 1.0 ml of a solution containing 0.05 M borate, 30 ug/ml potassium cyanide, 0.03 mg/ml dextran (MW=70,000), 0.15 mg/ml human serum albumin ($B_{12}$/Folate free), 0.2% thimerosal, 1.0 ug/ml hydrolyzed cyanocobolamin, 0.1% dithiothreitol and 0.02% ethylenediamine tetracetic acid at a pH of 9.3. The samples are heated in glass test tubes for 15 minutes in a boiling water bath, then re-equilibrated to ambient temperature. The sample is quantitatively transferred to a polystyrene sample cup and placed on a radioassay instrument. To the sample, 110 ul of a solution containing purified intrinsic factor at a level such that 50–70% of the $^{57}Co$-$B_{12}$ trace label is bound, folate milk binder at a level such that 55–75% of the $^{125}I$-pteroylglutamic acid (PGA) trace label is bound, 0.015 M boric acid, 0.0014 M sodium borate, 0.12% dextran (MW=70,000), 0.07% sodium chloride, 0.008% thimerosal and 0.06% human serum albumin ($B_{12}$/Folate-free) at a pH of 8.0 are added.

Next, 125 ul of a solution containing $^{57}Co$-labeled vitamin $B_{12}$ at 0.088 uCi/ml (specific activity=100–300 uCi/ug), $^{125}I$-labeled tyramine-pteroylglutamic acid at 0.26 uCi/ml (specific activity=1–2 mCi/ug), 0.05 M borate, 30 ug/ml potassium cyanide, 0.03 mg/ml dextran (MW=70,000), and 0.15 mg/ml human serum albumin ($B_{12}$/Folate free, heat denatured) at a pH of 9.3 is added. All samples are incubated for 30 minutes under ambient conditions. After incubation, 0.96 mls of the treated sample is flowed through a teflon chamber containing 95 mg of octadecylsilane (ODS) covalently bonded to silica gel particles (55–105 microns).

The internal dimensions of the cylindrical chamber cavity are 12 mm in length with a diameter of 4 mm. Covering the bottom of the chamber cavity is a 0.3 inch circle of 25 micron mesh nylon. The ODS is poured dry into the cavity and covered with a teflon wool circle 4 mm in diameter and 2 mm in thickness. The cavity top is then covered with another 0.3 inch circle of 25 micron mesh nylon. The ODS contained in the cavity constitutes a cylindrical column 4 mm in diameter and 10 mm in height. The entire sample flows through the ODS at a rate of 8.0 ml/minute. This results in the adsorption of the non-protein bound vitamin $B_{12}$ and Folic Acid (labeled and unlabeled) to the ODS while the protein-bound fraction continues into the radiodetector flow-cell where it is quantitated. This protein-bound fraction is rinsed into the detector for quantitation using a buffer containing 0.02 M phosphate, pH 7.4; 0.05 M sodium chloride; 0.005% gentamicin sulfate; and 0.003 M sodium azide at a rate of 3.0 ml/minute for 0.63 minutes.

The adsorbed fractions are eluted with a solution containing 0.025 M glycine, 0.025% benzoic acid, 0.0425 M phosphoric acid and 50% acetonitrile at a pH of 2.0 at a rate of 2.0 ml/minute for 0.89 minutes. These desorbed fractions are rinsed into the solid scintillation detector for quantitation with a solution containing 0.02 M phosphate, pH 7.4, 0.05 M sodium chloride; 0.005% gentamicin sulfate; and 0.003 M sodium azide at a rate of 3.0 ml/ minute for 0.4 minutes. This rinse prepares the ODS to receive the next cycling of sample. Vitamin $B_{12}$ and folate levels are determined by comparison of binding of samples to that of a known standard curve. Known amounts of vitamin $B_{12}$ and folate levels are determined by comparison of binding of samples to that of a known standard curve. Known amounts of vitamin $B_{12}$ and PGA are added to a solution containing 7% human serum albumin ($B_{12}$/Folate free), 0.005% chloramphenicol, 0.005% bacitracin, 0.001% nystatin, 0.9% sodium chloride, 0.05 M borate at a pH of 8.8. Typical results for vitamin $B_{12}$ include 54.2% binding at trace levels, 51.8% at 100 pg/ml, 44.4% at 200 pg/ml, 37.5% at 400/pg/ ml, 27.5% at 800 pg/ml and 18.8% at 1600 pg/ml.

Using the above curve, a control serum with an established range of 595 pg/ml to 847 pg/ml assayed at 716 pg/ml. Another control serum with a range of 234 pg/ml to 342 pg/ml assayed at 282 pg/ml. A third control serum with a range of 377 pg/ml to 557 pg/ml assayed at 487 pg/ml. Typical results for folate include trace binding of 61.6%, 53.4% at 1.0 ng/ml, 44.5% at 2.0 ng/ml, 35.0% at 4.0 ng/ml, 24.5% at 8.0 ng/ml, and 18.7% at 16.0 ng/ml. Utilizing the above curve, a control serum with an established range of 6.6 ng/ml to 8.8 ng/ml assayed at 7.9 ng/ml. Another control serum with an established range of 2.0 ng/ml to 2.8 ng/ml assayed at 2.2 ng/ml. A third control serum with an established range of 6.2 ng/ml to 8.6 ng/ml assayed at 7.8 ng/ml.

EXAMPLE 2

Digoxin

The determination of digoxin is accomplished by adding 50 ul of serum or test sample to a polystyrene sample cup. Added to the sample is 50 ul of a solution containing rabbit digoxin-specific antiserum at a level such that 55–80% of the $^{125}$I-Digoxin trace label is bound, 0.02 M phosphate, 0.05 M sodium chloride, 0.02% sodium azide, 0.005% gentamicin sulfate and 1.0% of normal rabbit serum at a pH of 7.4. This is followed by the addition of 100 ul of a solution containing $^{125}$I-labeled digoxigen-3-hemisuccinyl-tyrosine at 0.345 uCi/ml (specific activity=0.5–2 mCi/ug), 0.2 M phosphate, 0.5 M sodium chloride, 0.02% sodium azide, 0.005% gentamicin sulfate, and 0.2% salicylic acid at pH 7.4. This is then followed by 280 ml of a solution containing 0.02 M phosphate, pH 7.4, 0.05 M sodium chloride, 0.02% sodium azide, and 0.005% gentamicin sulfate. All samples are incubated for 18 minutes under ambient conditions. After incubation, the entire 0.48 ml of the incubated sample is flowed through a Teflon chamber containing 95 mg of octadecylsilane (ODS) covalently bonded to silica gel particles (55 to 105 microns). The internal dimensions of the chamber cavity are 12 mm in length with a diameter of 4 mm. Covering the bottom of the cavity is a 0.3-inch circle of 25 micron mesh nylon. The ODS is poured dry into the cavity and covered with a Teflon wool circle 4 mm in diameter and 2 mm in thickness. The cavity top is then covered with another 0.3-inch circle of 25 micron mesh nylon (the ODS contained in the cavity constitutes a cylindrical column 4 mm in diameter and 10 mm in height). The entire sample flows through the ODS at a rate of 8.0 ml/min. This results in the adsorption of the non-antibody bound digoxin (labeled and unlabeled) to the ODS while the antibody-bound fraction continues into the radiodetection flow-cell, where it is quantitated. The antibody-bound fraction is rinsed into the detector for quantitation using a buffer containing 0.02 M phosphate, pH 7.4, 0.05 M sodium chloride, 0.003 M sodium azide, and 0.005% gentamicin sulfate at a rate of 2.4 ml/min for 0.38 minutes. The adsorbed fractions are eluted with a solution containing 0.025 M glycine, 0.025% benzoic acid, 0.0425 M phosphoric acid and 50% acetonitrile at a pH of 2.0 at a rate of 2.4 ml/minute for 1.03 minutes. This desorbed fraction is rinsed into the solid scintillation detector for quantitation with a solution containing 0.02 M phosphate, pH 7.4, 0.05 M sodium chloride, 0.003 M sodium azide and 0.005% gentamicin sulfate at a rate of 3.0 ml/minute for 0.15 minute. This rinse prepares the ODS to receive the next cycling of the sample.

Digoxin levels are determined by comparison of binding of samples to that of a known standard curve. Known amounts of digoxin are added to a solution containing 99% Digoxin-free freon-treated plasma, 1.0% double-distilled water, 0.005% bacitracin and 0.005% chloramphenicol. Typical results for digoxin include 65.5% binding at trace levels, 55.3% at 0.5 ng/ml, 45.1% at 1.0 ng/ml, 32.8% at 2.0 ng/ml, 21.2% at 4.0 ng/ml, and 13.8% at 8.0 ng/ml. Using the above curve, a commercial control with an established range of 0.87 ng/ml–1.10 ng/ml assayed at 1.0 ng/ml. A second commercial control with an established range of 1.70 ng/ml 2.16 ng/ml assayed at 1.8 ng./ml . A third commercial control with an established range of 2.78 ng/ml–3.54 ng/ml assayed at 2.9 ng/ml.

EXAMPLE 3

$T_3$ Uptake

The determination of the uptake of triiodothyronine ($T_3$) by thyroid binding globulin (TBG) is accomplished by diluting 18 ul of a serum or test sample with 0.528 ml of a solution containing L-triiodothyronine-$^{125}$I, monoradioactive (specific activity =0.5–2 mCi/ug) at 0.07 uCi/ml, 0.01% bovine serum albumin, 1.7% propylene glycol, 0.05 M sodium chloride, 0.02 M phosphate, pH 7.4, 0.02% sodium azide and 0.005% gentamicin sulfate. The sample is incubated for 0.18 minutes under ambient conditions. After incubation, the entire 0.546 ml of sample is flowed through a Teflon chamber containing 95 mg of octadecylsilane (ODS) covalently bonded to silica gel particles (55–105 microns). The internal dimensions of the chamber cavity are 12 mm in length with a diameter of 4 mm. Covering the bottom of the cavity is a 0.3-inch circle of 25 micron mesh nylon. The ODS is poured dry into the cavity and covered with a Teflon wool circle 4 mm in diameter and 2 mm in thickness. The cavity top is then covered with another 0.3-inch circle of 25 micron mesh nylon (the ODS contained in the cavity constitutes a cylindrical column 4 mm in diameter and 10 mm in height). The entire sample flows through the ODS at a rate of 8.0 ml/min. This results in the adsorption of the non-TBG-bound $T_3$ (labeled and unlabeled) to the ODS while the protein-bound fraction continues into the radiodetection flow-cell, where it is quantitated. The protein-bound fraction is rinsed into the detector for quantitation, using a buffer containing 0.02 M phosphate, pH 7.4, 0.05 M sodium chloride, 0.003 M sodium azide and 0.005% gentamicin sulfate at a rate of 3.3 ml/min for 0.67 minutes. The adsorbed fractions are eluted with a solution containing 0.025 M glycine, 0.025% benzoic acid, 0.0425 M phosphoric acid, and 50% acetonitrile at a pH of 2.0 and at a rate of 3.30 ml/min for 0.50 minutes. The desorbed fraction is rinsed into the solid scintillation detector for quantitation with a solution containing 0.02 M phosphate, pH 7.4, 0.05 M sodium chloride, 0.003 M sodium azide, and 0.005% gentamicin sulfate at a rate of 3.30 ml/minute for 0.85 minutes. This rinse prepares the ODS to receive the next cycling of sample.

$T_3$ Uptake is determined by comparison of binding of samples to that of a known reference standard. The reference standard contains defibrinated plasma, stabilized $T_4$-free serum, 0.005% bacitracin, and 0.005% chloramphenicol. The standard is formulated such that the % binding is within 1.5% of a known primary reference standard. Typical results for $T_3$ Uptake include 30.4% binding for a reference sample and 31.6% binding for a reference sample. A known serum sample with a $T_3$ Uptake range of 42.3–58.3 assayed at 51.8. A second known serum sample with a $T_3$ Uptake range of 44.0–60.0 assayed at 51.2. A third known serum sample with a $T_3$ Uptake range of 23.5–39.5 assayed at 25.5.

EXAMPLE 4

Thyroxine

The determination of thyroxine (T4) is accomplished by adding 50 ul of serum or test sample which has been diluted 1/50 with a solution containing 0.01% Bovine serum albumin, 0.5 M glycine, 5.0% ethyl alcohol, 0.02% sodium azide and 0.03% 8-anilino-1-napthalene sulfonic acid (ammonium salt) at a pH of 10.5 into a polystyrene sample cup. Added to the sample is 50 ul of a solution containing rabbit thyroxine-specific antiserum at a level such that 40–70% of the $^{125}$I-T4 trace label is bound, 0.01% Bovine serum albumin, 0.5 M glycine, 5.0% ethyl alcohol, 0.02% sodium azide, and 0.03% 8-anilino-1-napthalene sulfonic acid (ammonium salt) at a pH of 10.5. This is followed by the addition of 100 ul of a solution containing L-thyroxine-$^{125}$I, mono-radioactive (specific activity 0.5–2.0 mCi/ug) at 0.2 uCi/ml, 0.009% Bovine serum albumin, 0.45 M glycine, 0.005 M phosphate, 5% propylene glycol, 4.5% ethyl alcohol, 0.018% sodium azide, and 0.027% 8-anilino-1-napthalene sulfonic acid (ammonium salt) at a pH of 10.5. This is then followed by 280 ul of a solution containing 0.02 M phosphate, pH 7.4, 0.05 M sodium chloride, 0.02% sodium azide and 0.005% gentamicin sulfate. All samples are incubated for 60 minutes under ambient conditions. After incubation the entire 0.48 ml of incubated sample is flowed through a Teflon chamber containing 95 mg of octadecylsilane (ODS) covalently bonded to silica gel particles (55 to 105 microns). The internal dimensions of the chamber cavity are 12 mm in length with a diameter of 4 mm. Covering the bottom of the cavity is a 0.3-inch circle of 25 micron mesh nylon. The ODS is poured dry into the cavity and covered with a Teflon wool circle 4 mm in diameter and 2 mm in thickness. The cavity top is then covered with another 0.3-inch circle of 25 micron mesh nylon (the ODS contained in the cavity constitutes a cylindrical column 4 mm in diameter and 10 mm in height). The entire sample flows through the ODS at a rate of 8.0 ml/min.

This results in the adsorption of the non-antibody bound thyroxine (labeled and unlabeled) to the ODS while the antibody-bound fraction continues into the radiodetection flow-cell, where it is quantitated. The antibody-bound fraction is rinsed into the detector for quantitation using a buffer containing 0.02 M phosphate, pH 7.4, 0.05 M sodium chloride, 0.003 M sodium azide, and 0.005% gentamicin sulfate at a rate of 2.4 ml/min. for 0.38 minutes. The adsorbed fractions are eluted with a solution containing 0.025 M glycine, 0.025% benzoic acid, 0.0425 M phosphoric acid and 50% acetonitrile at a pH of 2.0 at a rate of 2.4 ml/minute for 1.03 minutes. This desorbed fraction is rinsed into the solid scintillation detector for quantitation with a solution containing 0.2 M phosphate, pH 7.4, 0.05 M sodium chloride, 0.003 M sodium azide and 0.005% gentamicin sulfate at a rate of 3.0 ml/minute for 0.15 minute. This rinse prepares the ODS to receive the next cycling of the sample.

Thyroxine levels are determined by comparison of binding of samples to that of a known standard curve. Known amounts of thyroxine are added to a solution containing 99% thyroxine-free freon-treated plasma, 1.0% double-distilled water, 0.005% bacitracin and 0.005% chloramphenicol. Typical results for thyroxine include 46.4% binding at trace levels, 43.8% binding at 0.2 ng/ml and 41.2% binding at 0.4 ng/ml, 37.7% binding at 0.8 ng/ml, 34.1% binding at 1.6 ng/ml, 29.3% binding at 3.2 ng/ml, 26.1% binding at 6.4 ng/ml, and 25.0% binding at 12.8 ng/ml. Using the above curve, a commercial control with a range of 0.56–0.84 ng/ml assayed at 0.58 ng/ml. A second commercial control with a range of 1.41–2.11 ng/ml assayed at 1.51 ng/ml. A third commercial control with a range of 2.44–3.67 ng/ml assayed at 2.43 ng/ml.

EXAMPLE 5

Cortisol

The determination of cortisol is accomplished by adding 16 ul of serum or test sample to a polystyrene sample cup. Added to the sample is 50 ul of a solution containing $^{125}$I-labeled cortisol-carboxymethoxime-tyrosince at 0.4 uCi/ml (specific activity=0.5–2 mCi/ug), 0.02 M phosphate, pH 7.4, 0.05 M sodium chloride, 0.3 mg/ml 8-anilino-1-naphthalene sulfonic acid (ammonium salt), 0.003 M sodium azide and 0.005% gentamicin sulfate. This is followed by the addition of 100 ul of a solution containing rabbit cortisol-specific-antiserum at a level such that 50–80% of the $^{125}$I-Cortisol trace label is bound, 0.5 M phosphate, pH 6.0, 0.003 M sodium azide, 0.005% gentamicin sulfate, and 0.3 mg/ml 8-anilino-1-napthalene sulfonic acid (ammonium salt). This is then followed by the addition of 600 ul of a solution containing 0.02 M phosphate, pH 7.4, 0.05 M sodium chloride, 0.02% sodium azide, and 0.005% gentamicin sulfate. All samples are incubated for 30 minutes under ambient conditions. After incubation, the entire 0.72 ml of the incubated sample is flowed through a Teflon chamber containing 95 mg of octadecylsilane (ODS) covalently bonded to silica gel particles (55 to 105 microns). The internal dimensions of the chamber cavity are 12 mm in length with a diameter of 4 mm. Covering the bottom of the cavity is a 0.3-inch circle of 25 micron mesh nylon. The ODS is poured dry into the cavity and covered with a Teflon wool circle 4 mm in diameter and 2 mm in thickness. The cavity top is then covered with another 0.3-inch circle of 25 micron mesh nylon (the ODS contained in the cavity constitutes a cylindrical column 4 mm in diameter and 10 mm in height). The entire sample flows through the ODS at a rate of 8.0 ml/min.

This results in the adsorption of the non-antibody bound cortisol (labeled and unlabeled) to the ODS while the antibody-bound fraction continues into the radiodetection flow-cell, where it is quantitated. The antibody-bound fraction is rinsed into the detector for quantitation using a buffer containing 0.02 M phosphate, pH 7.4, 0.05 M sodium chloride, 0.003 M sodium azide, and 0.005% gentamicin sulfate at a rate of 2.4 ml/min. for 0.38 minutes. The adsorbed fractions are eluted with a solution containing 0.025 M glycine, 0.025% benzoic acid, 0.0425 M phosphoric acid and 50% acetonitrile at a pH of 2.0 at a rate of 2.4 ml/minute for 1.03 minutes. This desorbed fraction is rinsed into the solid scintillation detector for quantitation with a solution containing 0.02 M phosphate, pH 7.4, 0.05 M sodium chloride, 0.003 M sodium azide, and 0.005% gentamicin sulfate at a rate of 3.0 ml/minute for 0.15 minute. This rinse prepares the ODS to receive the next cycling of the sample.

Cortisol levels are determined by comparison of binding of samples to that of a known standard curve. Known amounts of cortisol are added to a solution containing 99% cortisol-free freon-treated plasma, 1.0% double-distilled water, 0.005% bacitracin and 0.005% Chloramphenicol. Typical results for cortisol include 70.6% binding at trace levels, 62.5% at 20 ug/dl, 55.5% at 4.0 ug/dl, 46.1% at 8.0 ug/dl, 35.6% at 16.0 ug/dl, 27.0% at 32.0 ug/dl, and 20.3% at 64.0 ug/dl. Using the above curve, a commercial control with an established range of 2.81 ug/dl-4.21 ug/dl assayed at 3.41 ug/dl. A second commercial control with an established range of 9.72 ug/dl-14.58 ug/dl assayed at 11.48 ug/dl. A third commercial control with an established range of 31.26 ug/dl-41.88 ug/dl assayed at 32.42 ug/dl.

EXAMPLE 6

Insulin

The determination of insulin is accomplished by adding 200 ul of serum or test sample to a polystyrene sample cup. Added to the sample is 75 ul of a solution containing guinea pig insulin-specific antiserum such that 50–80% of the $^{125}$I-Insulin trace label is bound, 0.025 M phosphate, pH 6.2, 0.02% Bovin serum albumin, 0.02% thimerosal and 60 KIU/ml trasylol. This is followed by the addition of 100 ul of a solution containing $^{125}$I-labeled insulin at 0.025 uCi/ml (specific activity 0.3–0.35 mCi/ug), 0.025 M phosphate, pH 6.2, 0.2% Bovine serum albumin, 0.02% thimerosal, and 60 KIU/ml trasylol and 1% acetonitrile. This is then followed by 280 ul of a solution containing 0.02 M phosphate, 0.05 M sodium chloride, 0.2% sodium azide, and 0.005% gentamicin sulfate at a pH of 7.4. All samples are incubated for 1.8 hours under ambient conditions. After incubation, the entire 655 ul of the incubated sample is flowed through a Teflon chamber containing 95 mg of octadecylsilane (ODS) covalently bonded to silica gel particles (55 to 105 microns). The internal dimensions of the chamber cavity are 12 mm in length with a diameter of 4 mm. Covering the bottom of the cavity is a 0.3-inch circle of 25 micron mesh nylon. The ODS is poured dry into the cavity and covered with a Teflon wool circle 4 mm in diameter and 2 mm in thickness. The cavity top is then covered with another 0.3-inch circle of 25 micron mesh nylon (the ODS contained in the cavity constitutes a cylindrical column 4 mm in diameter and 10 mm in height). The entire sample flows through the ODS at a rate of 8.0 ml/min.

This results in the adsorption of the non-antibody bound insulin (labeled and unlabeled) to the ODS while the antibody-bound fraction continues into the radiodetection flow-cell, where it is quantitated. The antibody-bound fraction is rinsed into the detector for quantitation using a buffer containing 0.02 M phosphate, pH 7.4, 0.05 M sodium chloride, 0.003 M sodium azide, and 0.05% gentamicin sulfate at a rate of 2.4 ml/min. for 0.38 minutes. The adsorbed fractions are eluted with a solution containing 0.025 M glycine, 0.025% benzoic acid, 0.0425 M phosphoric acid and 50% acetonitrile at a pH of 2.0 at a rate of 2.4 ml/minute for 1.03 minutes. This desorbed fraction is rinsed into the solid scintillation detector for quantitation with a solution containing 0.02; M phosphate, pH 7.4, 0.05 M sodium chloride, 0.003 M sodium azide, and 0.005% gentamicin sulfate at a rate of 3.0 ml/minute for 0.15 minute. This rinse prepares the ODS to receive the next cycling of the sample.

Insulin levels are determined by comparison of binding of samples to that of a known standard curve. Known amounts of insulin are added to a solution containing 99% insulin-free human serum. Typical results for insulin included 72.2% binding at trace levels, 62.4% binding at 8 uU/ml, and 61.9% binding at 16 uU/ml, 55.7% binding at 32 uU/ml, 51.7% binding at 63 uU/ml, 44.5% binding at 125 uU/ml and 38.2% binding at 250 uU/ml. Using the above curve, a commercial control with a range of 4.9–18.8 uU/ml assayed at 13.0 uU/ml. A second commercial control with a range of 24–52 uU/ml assayed at 43.1 uU/ml.

EXAMPLE 7

T$_3$ RIA

The determination of triiodothyronine is accomplished by adding 75 ul of serum or test sample to a polystyrene sample cup. Added to the sample is 50 ul of a solution containing rabbit triiodothyronine (T$_3$)-specific antiserum at a level such that 55–85% of the $^{125}$I-T$_3$ trace label is bound, 0.02 M phosphate, 0.05 M sodium chloride, 0.02% sodium azide, 0.005% gentamicin sulfate and 1.0% of normal rabbit serum at a pH of 7.4. This is followed by the addition of 300 ul of a solution containing $^{125}$I-labelled L-triiodothyronine -$^{125}$I, mono-radioactive (specific activity=0.5-2 mCi/ug) at 0.12 uCi/ml, 0.05 M tris (hydroxymethyl) aminomethane, 0.1 M glycine, 0.01% Bovine serum albumin, 0.04% sodium azide, 5.0% absolute ethanol (denatured) and 0.1% 8-anilino-1-napthalene sulfonic acid at a pH of 8.7. This is then followed by 75 ul of a solution containing 0.02 M phosphate, pH 7.4, 0.05 M sodium chloride, 0.02% sodium azide, and 0.005% gentamicin sulfate. All samples are incubated for 25 minutes under ambient conditions. After incubation, the entire 0.5 mls of the incubated sample is flowed through a Teflon chamber containing 95 mg of octadecylsilane (ODS) covalently bonded to silica gel particles (55–105 microns). The internal dimensions of the chamber cavity are 12 mm in length with a diameter of 4 mm. Covering the bottom of the cavity is a 0.3-inch circle of 25 micron mesh nylon. The ODS is poured dry into the cavity and covered with a Teflon wool circle 4 mm in diameter and 2 mm in thickness. The cavity top is then covered with another 0.3-inch cirlce of 25 micron mesh nylon. (The ODS contained in the cavity constitutes a cylindrical column 4 mm in diameter and 10 mm in height). The entire sample flows through the ODS at a rate of 8.0 ml/min.

This results in the adsorption of the non-antibody bound T$_3$ (labeled and unlabeled) to the ODS while the antibody-bound fraction continues into the radiodetection flow-cell, where it is quantitated. The antibody-bound fraction is rinsed into the detector for quantitation using a buffer containing 0.02 M phosphate, pH 7.4, 0.05 M sodium chloride, 0.003 M sodium azide, and 0.005% gentamicin sulfate at a rate of 2.4 ml/min for 0.38 minutes. The adsorbed fractions are eluted with a solution containing 0.025 M glycine, 0.025% benzoic acid, 0.0425 M phosphoric acid and 50% acetonitrile at a pH of 2.0 at a rate of 2.4 ml/minute for 1.03 minutes. This desorbed fraction is rinsed into the solid scintillation detector for quantitation with a solution containing 0.02 M phosphate, pH 7.4, 0.05 M sodium chloride, 0.003 M sodium azide, and 0.005% gentamicin sulfate at a rate of 3.0 ml/minute for 0.15 minute. This rinse prepares the ODS to receive the next cycling of the sample.

T$_3$ levels are determined by comparison of binding of samples to that of a known standard curve. Known amounts of T$_3$ are added to a solution containing 67% T$_4$-free human serum, 2% human serum albumin, 0.005% chloramphenicol, 0.005% bacitracin, and 0.003

M sodium azide. Typical results for triiodothyronine include 73.4% binding at trace levels, 67.9% binding at 50 ng/dl, 61.8% binding at 100 ng/dl, 52.2% binding at 200 ng/dl, 42.9% binding at 400 ng/dl, and 33.8% binding at 800 ng/dl. Using the above curve, a commercial control with an established range of 78–94 ng/dl assayed at 86 ng/dl. A second commercial control with an established range of 146–172 ng/dl assayed at 164 ng/dl. A third commercial control with an established range of 335–417 ng/dl assayed at 396 ng dl.

What is claimed is:

1. An improved competitive protein binding assay comprising;
    incubating an analyte in the presence of labeled analyte and a protein binder suitable for competitive binding activity by said analyte and said labeled analyte to provide a mixture having free analyte, free labeled analyte, bound analyte and bound labeled analyte,
    substantially separating said bound analyte and said bound labeled analyte from said free analyte and free labeled analyte to form a first fraction containing substantially said bound analyte and said bound labeled analyte and a second fraction containing substantially said free analyte and said free labeled analyte by causing a predetermined level of said mixture to flow through a bed of an organosilane coupled to silica gel, and
    detecting the labeled analyte of at least one of said first and second fractions to determine the concentration of said analyte by comparison to a reference.

2. An assay in accordance with claim 1 wherein said organosilane has an aliphatic $C_8$ to $C_{24}$ organic moiety.

3. An assay in accordance with claim 1 wherein said organosilane is octadecylsilane.

4. An assay in accordance with claim 1 wherein said silica gel has a particle size of from about 25 to about 250 microns.

5. An assay in accordance with claim 1 wherein said mixture is flowed through said bed of an organosilane coupled to silica gel at a flow rate of from about 0.02 to about 0.20 ml per cc of organosilane-silica gel per minute.

6. An assay in accordance with claim 1 wherein said mixture is flowed through said bed of an organosilane coupled to silica gel at a flow rate of from about 0.07 to about 1.0 ml per cc of organosilane-silica gel per minute.

7. An assay in accordance with claim 3 wherein said mixture is flowed through said bed of an organosilane coupled to silica gel at a flow rate of from about 0.02 to about 0.20 ml per cc of organosilane-silica gel per minute.

8. An assay in accordance with claim 3 wherein said mixture is flowed through said bed of an organosilane coupled to silica gel at flow rate of from about 0.07 to about 0.1 ml per cc of organosilane-silica gel per minute.

9. An assay in accordance with claim 1 wherein said analyte is selected from the group consisting of Digoxin, $T_3$, Thyroxine, Cortisol, Insulin, Folate, Vitamin $B_{12}$, and mixed Folate and Vitamin $B_{12}$.

10. An assay in accordance with claim 3 wherein said analyte is selected from the group consisting of Digoxin, $T_3$, Thyroxine, Cortisol, Insulin, Folate, Vitamin $B_{12}$, and mixed Folate and Vitamin $B_{12}$.

11. An assay in accordance with claim 1 wherein said assay is used for the simultaneous determination of folate and vitamin $B_{12}$.

12. An assay in accordance with claim 3 wherein said assay is used for the simultaneous determination of folate and vitamin $B_{12}$.

13. An assay in accordance with claims 1, 2 or 3 wherein said bed of an organosilane coupled to silica gel is recycled in an automated assay system.

* * * * *